United States Patent [19]

Keller

[11] Plant 5,235

[45] May 22, 1984

[54] DISTINCT VARIETY OF STREPTOCARPUS NAMED SUSI

[75] Inventor: Emil Keller, Hedingen, Switzerland

[73] Assignee: Oglevee Associates, Inc., Connellsville, Pa.

[21] Appl. No.: 452,818

[22] Filed: Dec. 28, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Webb, Burden, Robinson & Webb

[57] ABSTRACT

The new cultivar is generally characterized by a compact bouquet of bloom on top of the plant. The new cultivar exhibits vigorous plant growth and is a prolific bloomer. In addition, the new cultivar exhibits a more vivid red color as compared to other red varieties.

1 Drawing Figure

BACKGROUND OF THE NEW PLANT

The present invention comprises a new and distinct cultivar of *Streptocarpus* × *hybridus* known by the varietal name of Susi. The new cultivar was developed in a breeding program and is a cross of the varieties Rubina 31 (pollen parent) and Rot 41 (seed parent). The new cultivar is distinguished from its parentage by its persistent flower color, early blooming, short leaves, bright yellow throat and abundant blooming.

The new cultivar is generally characterized by a compact bouquet of bloom on top of the plant. The new cultivar exhibits vigorous plant growth and is a prolific bloomer. In addition, the new cultivar exhibits a more vivid red color as compared to other red varieties.

The new cultivar was discovered in 1979 in Hedingen, Switzerland; was first asexually reproduced by cuttings in Hedingen, Switzerland; and has been repeatedly asexually reproduced by cuttings at Oglevee Floral Company in Connellsville, Pa. It has been found to retain its distinctive charcteristics through successive propagations.

The new cultivar, when grown in a greenhouse in Connellsville, Pa., has a response time of eight weeks. This response time is measured from a plantlet which is a well rooted young plant in a five centimeter pot to a flowering plant in a fifteen centimeter pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected from asexual reproductions carried out by the Oglevee Floral Company in Connellsville, Pa. The plant history was taken on eight week plants blossomed under natural light in a greenhouse and color readings were taken using natural light. Color references are primarily to the R.H.S. color chart of The Royal Horticultural Society of London. Some color reference is to Exotica III and such reference is duly noted.

Botanical classification: Gesneriaceae (family); *Streptocarpus* × *hybridus* (genus × species).

Flower:

*Fully expanded.*—6.35 Centimeters.

*Borne.*—In clusters of two to six flowers per flower stalk. Flower stalk arises from mid-rib of each leaf.

*Stem.*—Single, long and pubescent with some stems being flat shaped rather than round.

*Form.*—Funnel formed in an umbel.

*Permanence.*—Long lasting 21 to 25 days.

Color:

*Tonality from a distance.*—Predominantly beet purple to maroon with a yellow throat (Exotica III).

*Front of petals.*—Fan 2 Red Purple Group 66-A with veining being darker and more purple than balance of petal.

*Throat.*—Veined light and dark with the light being Fan 1 Yellow Group 8-D and the dark being Fan 1 Yellow Group 9-C.

*Reverse of petals.*—Fan 2 Red Purple Group 74-C.

*Discoloration.*—Insignificant.

Petals:

*Texture.*—Velvet.

*Appearance.*—Individually lobed with slightly serrated margin.

*Arrangement.*—Regularly united into an elliptical form.

*Persistence.*—Lives for 21 to 25 days and remains on plant in dry form until picked.

*Fragrance.*—None.

Reproductive organs:

*Anthers.*—Two per flower and interconnected.

*Filament.*—6 Centimeter and attaches to petal about 3 centimeters up from base.

*Pollen.*—Generally nonfertile.

*Style.*—1.25 Centimeters from top of ovary to a flattened stigma.

*Ovaries.*—Long and narrow, 1.5 centimeters long and 2 millimeters in diameter.

Plant:

*Form.*—Leaves rosette from a crown at the soil line.

*Growth.*—A spreading, free flowing habit with leaves being elliptical.

*Height from soil line.*—15 to 20 centimeters.

*Spread.*—25 to 35 centimeters.

Foliage:

*Top side.*—Fan 3 Green Group 137-A.

*Under side.*—Fan 4 Greyed Green Group 193-A.

*Size.*—15 to 22 centimeters in length and 5 to 10 centimeters wide at the widest point.
*Quantity.*—6 to 10 leaves.
*Shape.*—Elliptical.
*Ribs and veins.*—Pinnate.
*Ribs and vein color.*—Fan 3 Green Group 137-C.
*Margin.*—Cuneate.

*Leaf tips.*—Obtuse.
*Leaf base.*—Acute.

I claim:

1. A new and distinct variety of Streptocarpus substantially as herein shown and described.

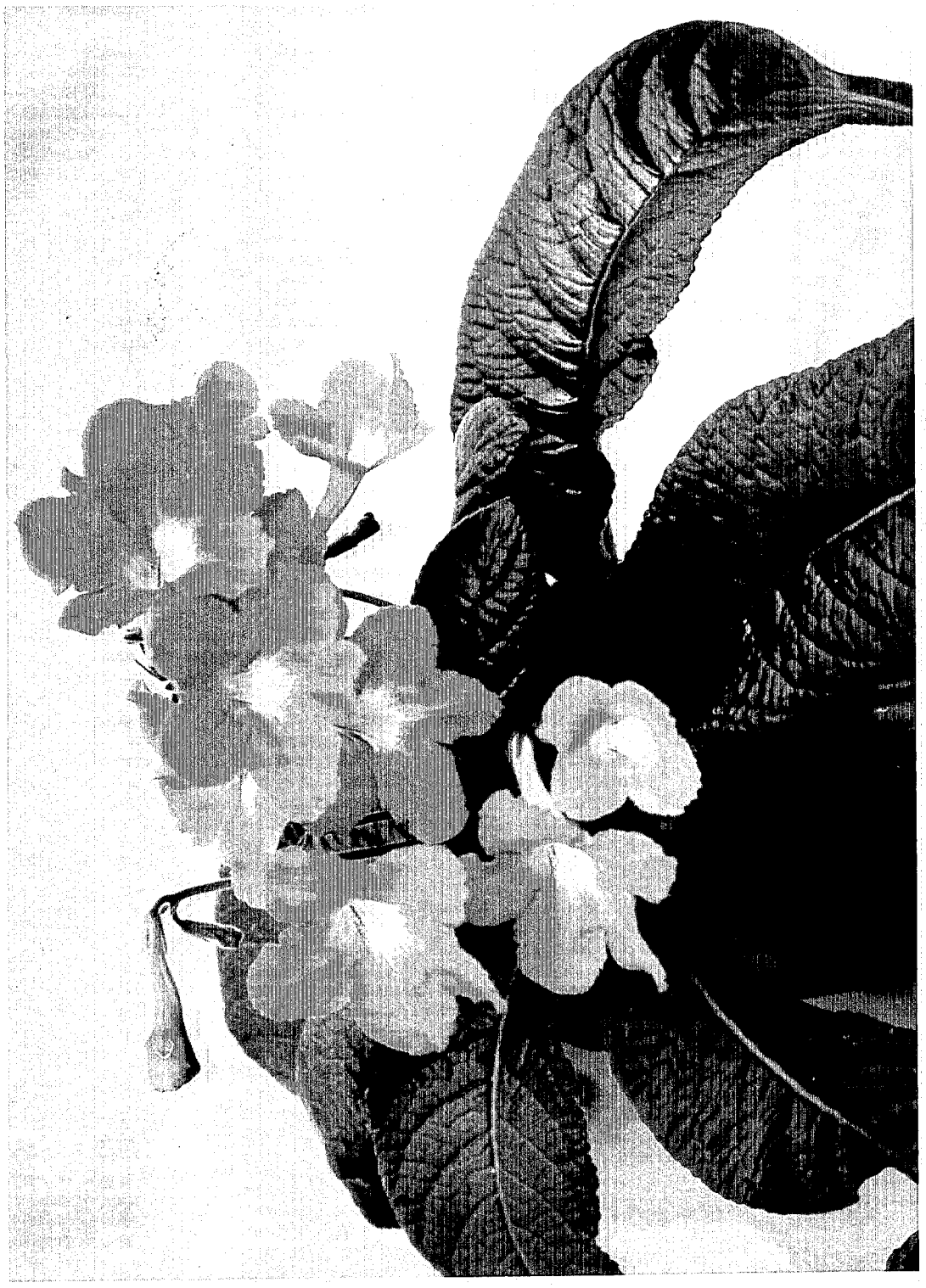

* * * * *